United States Patent

Clausen et al.

[11] Patent Number: 5,224,965
[45] Date of Patent: Jul. 6, 1993

[54] COMPOSITION FOR THE OXIDATIVE DYEING OF HAIR AND NEW 5-HALOGEN-2,4-DIAMINO ALKYLBENZENES

[75] Inventors: Thomas Clausen, Alsbach; Alexa Weinges, Heidelberg; Wolfgang R. Balzer, Alsbach, all of Fed. Rep. of Germany

[73] Assignee: Wella Aktiengesellschaft, Darmstadt, Fed. Rep. of Germany

[21] Appl. No.: 847,080
[22] PCT Filed: Aug. 17, 1991
[86] PCT No.: PCT/EP91/01565
  § 371 Date: Apr. 7, 1992
  § 102(e) Date: Apr. 7, 1992
[87] PCT Pub. No.: WO92/04005
  PCT Pub. Date: Mar. 19, 1992

[30] Foreign Application Priority Data

Sep. 10, 1990 [DE] Fed. Rep. of Germany ....... 4028661

[51] Int. Cl.$^5$ ............................................. A61K 7/13
[52] U.S. Cl. ............................................. 8/411; 8/405; 8/406; 8/407; 8/408; 8/429; 8/432; 424/70; 564/441; 564/442
[58] Field of Search ............... 8/405, 406, 407, 408, 8/411, 429, 432; 424/70; 132/208; 564/441, 442

[56] References Cited

U.S. PATENT DOCUMENTS 4,031,160 6/1977 Kalopissis ............................... 8/25

FOREIGN PATENT DOCUMENTS 0252351 1/1988 European Pat. Off. .
3622784 1/1988 Fed. Rep. of Germany .
3430513 2/1988 Fed. Rep. of Germany .
2542193 9/1984 France .
2054666 2/1981 United Kingdom .

OTHER PUBLICATIONS

J. C. Johnson "Hair Dyes", Apr. 1973 Noyes Data Corp. pp. 3–91, 113–139.
Chemische Berichte 33, 2505 (1900), F. Reverdin, et al.

Primary Examiner—Paul Lieberman
Assistant Examiner—William S. Parks
Attorney, Agent, or Firm—Michael J. Striker

[57] ABSTRACT

The composition for the oxidative dyeing of hair contains at least one coupler substance of the formula

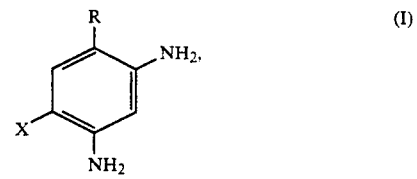

where R is a straight-chain or branched $C_1$- to $C_4$-alkyl group and X is fluorine or bromine, and new 5-halogen-2,4-diaminoalkylbenzenes.

The coupler substances of formula (I) are obtainable by simple chemical reactions, easily soluble in water and have a good shelf stability particularly as constituents of the hair dye composition described here.

In addition to the multitude of color shades, the dye results which can be achieved with the hair dye composition according to the invention are distinguished particularly by the intensity of color of the red tones and good uniformity of color of the blue tones.

11 Claims, No Drawings

COMPOSITION FOR THE OXIDATIVE DYEING OF HAIR AND NEW 5-HALOGEN-2,4-DIAMINO ALKYLBENZENES

BACKGROUND OF THE INVENTION

The subject matter of the invention is a composition for the oxidative dyeing of hair based on 5-halogen-2,4-diaminoalkylbenzenes as coupler substances and new 5-halogen-2,4-diaminoalkylbenzenes.

Oxidative dyestuffs have achieved considerable importance in hair dyeing practice. The dyes are produced by the oxidative coupling of developer substances and coupler substances in the hair shaft. This leads to very intensive dyeing of hair with very good color fastness. Moreover, various color shades can be produced by combining suitable developer and coupler substances.

2,5-diaminotoluene, 1,4-diaminobenzene, 2-(2'-hydroxyethyl)-1,4-diaminobenzene, 4-aminophenol, 4-amino-2-aminomethylphenol and 4-amino-3-methyl-phenol are preferred as developer substances.

The coupler substances which are preferably used are m-phenylenediamine and its derivatives, e.g. 2,4-diaminophenoxyethanol, 2,4-diaminobenzyl alcohol, 2-amino-4-(2'-hydroxyethyl)aminoanisole, or pyridine derivatives such as 3,5-diamino-2,6-dimethoxypyridine as blue coupler, 1-naphthol, m-aminophenol and its derivatives such as 2-amino4-chloro-6-methylphenol, 3-amino-2-methylphenol, 4-amino-2-hydroxyphenoxyethanol and 3-amino-5-hydroxy-2,6-dimethoxypyridine as red coupler, as well as resorcinol, 4-chlororesorcinol, 4,6-dichlororesorcinol, 2-methylresorcinol, 4-hydroxy-1,2-methylenedioxybenzene, 4-(2'-hydroxyethyl)amino-1,2-methylenedioxybenzene and 4-hydroxyindole as couplers for the brown to blond range.

Numerous special demands are made on oxidative dyestuffs used for dyeing human hair. The dyes must be unobjectionable in toxicological and dermatological respects and must enable the desired intensity of coloring. Further, a good fastness to light, permanent waving, acids and rubbing is required of the achieved hair dyes. But in every case such hair dyes must remain stable over a period of at least 4 to 6 weeks without being influenced by light, rubbing or chemical agents. Moreover, it is required that a wide assortment of different shades of color can be produced by combining suitable developer and coupler components.

However, the coupler substances presently used in hair dye compositions for producing red and clear blue color tones in particular cannot meet the aforementioned demands in a satisfactory manner.

The 5-chloro-2,4-diaminotoluene described by F. Reverdin and P. Crépieux in Chemische Berichte 33, 2505 (1900) produces pure blue dyeing results with developers of the p-phenylenediamine type; but only extremely weak reddish dyeing results are obtained with developers such as p-aminophenol or its derivatives.

The 2,4-diamino-5-tetrafluoroethoxytoluene known from DE-OS 34 30 513 shows no mutagenic effect in the Ames test, but the depths of color and light fastness of the dyeing results achieved with this coupler substance are not satisfactory.

The coupler substances 2,4-diamino-5-ethoxytoluene or 2,4-diamino-5-(2'-hydroxyethyl)oxytoluene described in DE-OS 36 22 784 possess good toxicological properties and good characteristics with respect to application technology. But the synthesis of these compounds, which is based on 3-hydroxy-4-nitrotoluene, is costly since five reaction steps must be carried out and is therefore unsatisfactory in view of the time required for synthesis (labor costs) and the energy costs.

SUMMARY OF THE INVENTION

Accordingly, the object of the invention is to provide a hair dye composition for the oxidative dyeing of hair based on developer substances conventionally used in hair dyeing containing new coupler substances which meets the aforementioned demands with respect to application technology characteristics and the production method of the new coupler substance.

In this regard it has now been found that the proposed object is met to an outstanding degree by a composition for the oxidative dyeing of hair based on a combination of developer and coupler substances, and possibly other dye components and ingredients conventionally used in hair dye compositions, containing at least one coupler substance of the formula

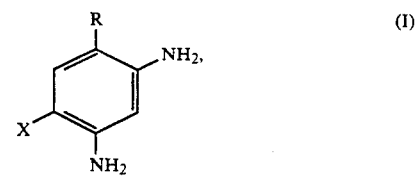

where R is a straight-chain or branched $C_1$- to $C_4$-alkyl group and X is fluorine or bromine, or its physiologically tolerated water-soluble salt.

The coupler substances of the general formula (I) can be obtained by simple chemical reactions from technically accessible base compounds and, together with developer substances such as p-phenylenediamine, produce clear blue dye results without a red cast. Color-saturated red dyeing whose intensity of color is even greater than that achieved in dyeing with the unsubstituted 2,4-diaminotoluene can be achieved with developer substances of the p-aminophenol type.

The coupler substances of the general formula (I) are easily soluble in water and have an outstanding shelf stability particularly as a constituent of the hair dye composition described here.

The coupler substances of formula (I) according to the invention are to be contained in the hair dye composition described here in a quantity sufficient for the dyeing of hair, preferably in a quantity of 0.01 to 5 percent by weight, particularly preferably 0.1 to 3 percent by weight.

Of the coupler substances of the general formula (I), 5-bromo-2,4-diaminotoluene and 5-fluoro-2,4-diaminotoluene are preferably contained in the hair dye composition.

Moreover, the hair dye composition can contain, in addition, 0.01 to 5 percent by weight, preferably 0.1 to 3 percent by weight, of at least one other coupler substance, e.g. resorcinol, 4-chlororesorcinol, 4,6-dichlororesorcinol, 2-methylresorcinol, 2-amino-4-(2'hydroxyethylamino)anisole, 2-amino-4-ethylaminoanisole, 2,4-diaminobenzyl alcohol, m-phenylenediamine, 5-amino-2-methylphenol 2,4-diaminophenoxyethanol, 1-naphthol, m-aminophenol, 3-amino-4-chloro-6-methylphenol, 3-amino-2-methylphenol, 4-amino-2hydroxyphenoxyethanol, 4-hydroxy-1,2-methylenedioxybenzene, 4-(2'-hydroxyethylamino)-

1,2-methylenedioxybenzene, 2,4-diamino-5-ethoxytoluene, 4-hydroxyindole, 3-amino-5-hydroxy2,6-dimethoxypyridine, and 3,5-diamino-2,6-dimethoxypyridine.

The developer substances coming under consideration as constituents of the hair dye composition according to the invention are chiefly 1,4-diaminobenzene, 2,5-diaminotoluene, 2,5-diaminobenzyl alcohol, 2-(2'-hydroxyethyl)-1,4-diaminobenzene, 4-aminophenol, 4-amino-2-aminomethylphenol, 4-amino-3-methylphenol, 4-amino-2-methoxymethylphenol, 4-amino-2-ethoxymethylphenol and tetraaminopyridine or their physiologically tolerated salts. The quantity of developer substances contained in the composition according to the invention is preferably 0.01 to 5 percent by weight, but 0.1 to 3.0 percent by weight is particularly preferred.

The conventional coupler and developer substances can be contained individually or in combination in the hair dye composition according to the invention. The total quantity of combined developer and coupler substances contained in the hair dye composition described here should be approximately 0.1 to 5.0 percent by weight, preferably 0.5 to 4.0 percent by weight.

The developer substances are generally used in approximately equimolar quantities with respect to the coupler substances. However, it is not disadvantageous if the proportion of developer substances exceeds or falls below that of the coupler substances.

Further, the hair dye composition of the present application can also contain other coloring components, e.g. 6-aminomethylphenol and 2-amino-5-methylphenol as well as conventional direct-dyeing dyestuffs, e.g. triphenylmethane dyestuffs such as Basic Violet 14 (C.I. 42,510) and Basic Violet 2 (C.I. 42,520), aromatic nitro dyes such as 2-nitro-1,4-diaminobenzene, 2-amino-4-nitrophenol, 2-amino-5-nitrophenol, 2-amino-4,6-dinitrophenol, 2-amino-5-(2'hydroxyethylamino)nitrobenzene and 4-(2'-hydroxyethylamino)-3-nitrotoluene, 1-(2'-ureidoethyl)amino-4-nitrobenzene and azo dyestuffs such as Acid Brown 4 (C.I. 14,805), and dispersed dyestuffs such as 1,4-diaminoanthraquinone and 1,4,5,8-tetraaminoanthraquinone.

Other suitable dyestuffs which are absorbed directly on the hair are described e.g. in the book by J. C. Johnson, "Hair Dyes", Noyes Data Corp., Park Ridge, USA (1973), pages 3-91 and 113-139 (ISBN: 0-8155-0477-2).

Of course, the coupler and developer substances and other dye components, insofar as they are bases, can also be used in the form of physiologically tolerated acid addition salts, e.g. as hydrochloride or sulfate or—insofar as they possess aromatic OH groups—in the form of salts with bases, e.g. as alkali phenolates.

The hair dye composition can also contain direct-dyeing dyestuffs and self-coupling preliminary dye stages in a quantity of 0.1 to 4.0 percent by weight.

Moreover, other conventional cosmetic ingredients can also be present in the hair dye compositions, e.g. antioxidants such as ascorbic acid, thiogylcolic acid or sodium sulfite, perfume oils, complexing agents, wetting agents, emulsifying agents, thickeners, hair care materials, etc.

The preparation form can be a solution for example, particularly an aqueous-alcoholic solution. However, a cream, gel or emulsion is particularly preferred as preparation form. Its composition is a mixture of dye components with ingredients conventionally used for such preparations.

Conventional ingredients in solutions, creams, emulsions or gels are e.g. solvents such as water, lower aliphatic alcohols, e.g. ethanol, propanol and isopropanol, or glycols such as glycerol and 1,2-propylene glycol, also wetting agents or emulsifying agents from the classes of anionic, cationic, amphoteric or nonionic surface-active substances such as fatty alcohol sulfates, ethoxylated fatty alcohol sulfates, alkyl sulfonates, alkylbenzenesulfonates, alkyltrimethylammonium salts, alkylbetaines, ethoxylated fatty alcohols, ethoxylated nonylphenols, fatty acid alkanol amides, ethoxylated fatty acid esters, also thickeners such as higher fatty alcohols, starch, cellulose derivatives, vaseline, paraffin oil and fatty acids, as well as hair care materials such as cationic resins, lanolin derivatives, cholesterol, pantothenic acid and betaine. The aforementioned constituents are used in amounts which are conventional for such purposes. For example, the wetting agents and emulsifying agents are used in concentrations of approximately 0.5 to 30 percent by weight, the thickeners are used in quantities of approximately 0.1 to 25 percent by weight, and the hair care materials are used in a concentration of approximately 0.1 to 5.0 percent by weight.

Depending on the composition, the hair dye composition according to the invention can react slightly acidic, neutral or alkaline. In particular, it has a pH value in the alkaline range of 8.0 to 11.5. It is preferably adjusted with ammonia. However, organic amines, e.g. monoethanolamine and triethanolamine, or inorganic bases such as sodium hydroxide and potassium hydroxide can also be used.

When used for the oxidative dyeing of hair, the hair dye composition described above is mixed immediately before use with an oxidizing agent and an amount of this mixture sufficient for the hair dyeing treatment, generally 60 to 200 g depending on the fullness of the hair, is applied to the hair.

Chiefly hydrogen peroxide or its addition compounds in urea, melamine or sodium borate in the form of 3- to 12-percent, preferably 6-percent, aqueous solutions come under consideration as oxidizing agents for the development of the hair dye.

If a 6-percent hydrogen peroxide solution is used as oxidizing agent, then the weight ratio between the hair dye composition and the oxidizing agent is 5:1 to 1:2, preferably 1:1. Greater amounts of oxidizing agent are used chiefly when there are higher dyestuff concentrations in the hair dye composition or when a more intensive bleaching of the hair is intended simultaneously.

The mixture is allowed to act on the hair at 15° to 50° C. for approximately 10 to 45 minutes, preferably 30 minutes. The hair is then rinsed with water and dried. After this rinsing the hair may be washed with shampoo if necessary and possibly re-rinsed with a weak organic acid such as citric acid or tartaric acid. The hair is then dried.

The hair dye composition according to the invention results in hair coloring with excellent fastness properties, particularly with respect to light, shampooing and rubbing, and can be removed again with reducing agents. As regards dyeing possibilities, the hair dye composition according to the invention offers a wide assortment of different color shades depending on the type and composition of the dye components. The great intensity of color in the reds which can be achieved and the uniformity of color of the blue coloring which can be achieved are noteworthy. Finally, hair which is graying and not already chemically damaged can be dyed easily and with very good covering power with the aid of the described hair dye composition. The colors which can be obtained in so doing can be reproduced very well and with uniformity regardless of varying hair structure.

The 5-halogen-2,4-diaminoalkylbenzenes of the general formula (I) can be produced simply and inexpensively from the corresponding 3-halogen alkyl benzenes, e.g. the technically available 3-fluorotoluene, in two synthesis steps by nitration in the 2,4-position and subsequent reduction of the nitro groups according to the following diagram, where R and X have the same meaning as above:

$$\text{(II)} \xrightarrow{} \text{(III)} \xrightarrow{} \text{(I)}$$

The nitration reagents conventionally used in organic synthesis are taken into consideration for nitration. A mixture of sulfuric acid and nitric acid is preferred. The reagents known for this synthesis step likewise come under consideration for the reduction of the nitro groups, e.g. hydrogen in the presence of a suitable catalyst.

The subject matter of the present application is also a new 5-halogen-2,4-diaminoalkylbenzene of the general formula (IV)

where $R^1$ is a straight-chain or branched $C_1$- to $C_4$-alkyl group and Y is fluorine or bromine, assuming that Y is not bromine if $R^1$ is the methyl group.

The 5-fluoro-2,4-diaminotoluene is mentioned as an example of the new compounds of formula (IV).

The following examples serve to explain the subject matter of the invention in more detail.

EXAMPLES

Example 1: Hair dye solution

```
0.80 g  5-fluoro-2,4-diaminotoluene
2.80 g  2-methyl-1,4-diaminobenzene sulfate
0.60 g  4-(2'-hydroxyethyl)amino-1,2-methylenedioxy-benzene
0.10 g  m-aminophenol
0.45 g  3-amino-5-hydroxy-2,6-dimethoxypyridine-
        hydrochloride
```

-continued

```
0.40 g   sodium sulfite, anhydrous
10.00 g  lauryl alcohol diglycol ether sulfate (28-
         percent aqueous solution)
10.00 g  isopropanol
20.00 g  ammonia (22-percent aqueous solution)
54.85 g  water
100.00 g
```

50 g of the hair dye solution described above are mixed with 50 ml of a 6-percent hydrogen peroxide solution immediately before use. The mixture is then applied to blond human hair. After allowing the mixture to act for a period of 30 minutes at forty degrees Celsius, the hair is rinsed with water and dried. The hair is dyed black.

Example 2: Hair dye composition in gel form

```
0.15 g   5-fluoro-2,4-diaminotoluene
1.10 g   2-(2'-hydroxyethyl-1,4-diaminobenzene-sulfate
0.20 g   resorcinol
0.05 g   m-aminophenol
0.40 g   sodium sulfite, anhydrous
15.00 g  oleic acid
7.00 g   isopropanol
10.00 g  ammonia (22-percent aqueous solution)
66.10 g  water
100.00 g
```

50 g of this hair dye composition in gel form are mixed with 50 ml of a 6-percent hydrogen peroxide solution shortly before use. The mixture is applied to blond human hair. After allowing the mixture to act for a period of thirty minutes at 40° Celsius the hair is rinsed with water and then dried. The hair has taken on a natural medium-blond color.

Example A: Production of 5-fluoro-2,4-diaminotoluene

Step 1: 5-fluoro-2,4-dinitrotoluene 5.5 g of 3-fluorotoluene are nitrated with a cooled mixture of 10.9 ml concentrated $H_2SO_4$ and 9.3 ml concentrated $HNO_3$. The mixture is stirred for a period of 24 hours at room temperature and then poured on ice. The precipitated product is washed with $H_2O$ accompanied by suction and, after recrystallization from alcohol, 5.8 g (58% of theory) of crystals colored a pale yellow and having a melting point of 80 degree Celsius are obtained.

$^1$H-NMR ($D_6$-DMSO):
$\delta = 2.64$ (s; 3 H, —$CH_3$)
7.85 (d; J=12 Hz, 1H, 6-H)
8.76 ppm (d; J=7.1 Hz, 1H, 3-H).
MS (70 eV): m/e=200 (M+)

Step 2: 5-fluoro-2,4-diaminotoluene 2 g (0.01 ml) of 5-fluoro-2,4-dinitrotoluene from Step 1 are hydrated with catalytic amounts of palladium/carbon (10% Pd) in 50 ml absolute ethanol. After the catalyst is removed by filtration, the solvent is distilled off completely and the obtained product is recrystallized from toluene. 0.7 g (50 % of theory) of 5-fluoro-2,4-diaminotoluene is obtained which melts at 112° Celsius accompanied by decomposition.

$^1$H-NMR ($D_6$-DMSO):
$\delta = 2.49$ (s; 3H, —$CH_3$)
4.36 (s; 2H, $NH_2$)
4.54 (s; 2H, $NH_2$)
6.03 (d; J=8.6 Hz, 3-H)
6.54 ppm (d; J=12 Hz, 6-H).

MS (70 eV): m/e=140 (M+).

All percentages given in the present application are percent by weight unless otherwise indicated.

While the invention has been illustrated and described as embodied in a composition for oxidative dyeing of hair and new 5-halogen-2,4-diaminoalkylbenzene, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

We claim:

1. Composition for oxidative dyeing of hair containing a combination of developer and coupler substances wherein the coupler substance includes an effective amount to modify said hair dyeing developer substances of at least one 5-halogen-2,4-diaminoalkylbenzene of the formula

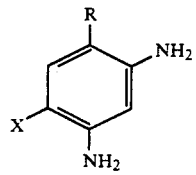

(I)

where R is a straight-chain or branched $C_1$ to $C_4$-alkyl group and X is fluorine or bromine, or physiologically tolerated water-soluble salts thereof, and also containing at least one conventional cosmetic ingredient selected from the group consisting essentially of antioxidants, perfume oils, complexing agents, wetting agents, emulsifying agents, thickeners and hair care materials.

2. Composition according to claim 1, containing the at least one 5-halogen-2,4-diaminoalkylbenzene of the formula (I) in a quantity of 0.01 to 5 percent by weight.

3. Composition according to claim 1, wherein the 5halogen-2,4-diaminoalkylbenzene of the formula (I) comprises 5-bromo-2,4-diaminotoluene.

4. Composition according to claim 1, wherein the 5-halogen-2,4-diaminoalkylbenzene of the formula (I) comprises 5-fluoro-2,4-diaminotoluene.

5. Composition according to claim 1, wherein the coupler substance includes at least one member selected from the group consisting of resorcinol, 4-chlororesorcinol, 4,6-dichlororesorcinol, 2-methylresorcinol, 2-amino-4-(2'-hydroxy-ethylamino)anisole, 2-amino-4-ethylaminoanisole, 2,4-diaminobenzyl alcohol, m-phenylenediamine, 5-amino-2-methylphenol, 2,4-diaminophenoxyethanol, 1-napthol, m-aminophenol, 3-amino-4-chloro-6-methylphenol, 3-amino-2-methylphenol, 4-amino-2-hydroxyphenoxyethanol, 4-hydroxy-1,2-methylenedioxybenzene, 4-(2'-hydroxyethylamino)-1,2-methylenedioxybenzene, 2,4-dimaino-5-ethoxytoluene, 4-hydroxyindole, 3-amino-5-hydroxy-2,6-dimethoxy-pyridine, and 3,5-diamino-2,6-dimethoxypyridine.

6. Composition according to claim 1, wherein the developer substance is selected from the group consisting of 1,4-diaminobenzene, 2,5-diaminotoluene, 2,5-diaminobenzyl alcohol, 2-(2'-hydroxyethyl)-1,4-diaminobenzene, 2-(2'-hydroxyethyl)-1,4-diaminobenzene, 4-aminophenol, 4-amino-2-aminomethylphenol, 4-amino-3-3-methylphenol, 4-amino-2-methyoxymethylphenol, 4-amino-2-ethoxymethylphenol, tetraaminopyrimidine and physiologicially tolerated salts thereof.

7. Composition according to claim 1, containing 0.1 to 5.0 percent by weight of the combination of the developer and coupler substances.

8. Composition according to claim 1, further comprising another dye component selected from the group consisting of 6-aminomethylphenol and 2-amino-5-methylphenol, Basic Violet 14 (C.I. 42,510), Basic Violet 2 (C.I. 42,520), 2-nitro-1,4-diaminobenzene, 2-amino-4-nitrophenol, 2-amino-5-nitrophenol, 2-amino-4,6-dinitrophenol, 2-amino-5-(2'-hydroxyethylamino)nitrobenzene, 4-(2'-hydroxyethylamino)-3-nitrotoluene, 1-(2'-ureidoethyl)-amino-4-nitrobenzene, Acid Brown 4 (C.I. 14,805), 1,4-diaminoanthraquinone and I,4,5,8-tetraaminoanthraquinone.

9. Composition according to claim 1, having a pH from 8 to 11.5.

10. 5-Halogen-2,4-diaminoalkylbenzene of the formula

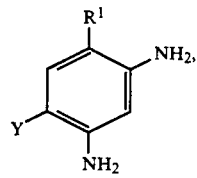

(IV)

where $R^1$ is a straight-chain or branched $C_1$- to $C_4$-alkyl group and Y is fluorine or bromine, assuming that Y is not bromine if $R^1$ is the methyl group.

11. 5-fluoro-2,4-diaminotoluene.

* * * * *